United States Patent
Han et al.

(10) Patent No.: US 7,476,776 B2
(45) Date of Patent: Jan. 13, 2009

(54) METHOD FOR IMPROVING GERMLINE TRANSMISSION EFFICIENCY OF AVIAN PRIMORDIAL GERM CELLS

(75) Inventors: Jae Yong Han, Seoul (KR); Tae Sub Park, Anyang-si (KR); Yeong Ho Hong, Suwon-si (KR); Se Chang Kwon, Seoul (KR)

(73) Assignees: Seoul National University Industry Foundation, Seoul (KR); Avicore Biotechnology Institute Inc., Gunpo, Kyunggi Province (KR); Hanmi Pharm. Co. Ltd., Kyunggi-Do (KR)

( * ) Notice: Subject to any disclaimer, the term of this patent is extended or adjusted under 35 U.S.C. 154(b) by 0 days.

(21) Appl. No.: 10/554,030

(22) PCT Filed: Apr. 21, 2004

(86) PCT No.: PCT/KR2004/000908

§ 371 (c)(1),
(2), (4) Date: Dec. 27, 2005

(87) PCT Pub. No.: WO2004/094627

PCT Pub. Date: Nov. 4, 2004

(65) Prior Publication Data

US 2006/0218657 A1        Sep. 28, 2006

(30) Foreign Application Priority Data

Apr. 21, 2003   (KR) ................. 10-2003-0025158

(51) Int. Cl.
*A01K 67/027*   (2006.01)
(52) U.S. Cl. ........................... 800/19; 435/325
(58) Field of Classification Search ............ 800/19; 435/325
See application file for complete search history.

(56) References Cited

FOREIGN PATENT DOCUMENTS

| WO | 94/07997 | 4/1994 |
|---|---|---|
| WO | 99/06534 | 2/1999 |
| WO | 03/024200 | 3/2003 |

OTHER PUBLICATIONS

Vick (Proc. R. Soc. Lond., 1993, vol. 251, p. 179-182).*
Allioli (Developmental Biol., 1994, vol. 165, p. 30-37).*
Thoroval (Transgenic Research, 1995. vol. 4, p. 369-376).*
Chang (Cell Biology International, 1995, vol. 19, No. 6, p. 143-149).*
Naito (Mar. 31-Apr. 5, 1996, 6th International Symposium on avian endocrinology, "Expression of exogenous DNA in embryonic gonads by transferring primordial germ cells transfected in vitro", p. 69-73).*
Naito (1998, J. Reproduction and Fertility, vol. 113, p. 137-143).*
Pain (Development. 1996, vol. 122, p. 2339-2348).*
Park (Mol. Reproduction and Development, 2000, vol. 56, p. 475-482).*
Zandong (Transgenic Research, Feb. 2002. vol. 11, No. 1, p. 85).*
Kim (Transgenic Research, Feb. 2002, vol. 11, No. 1, p. 85).*
Petitte (J. Poultry Sci., 4th quarter of 2002, vol. 39, No. 4. p. 205-228).*
Han (Theriogenology, Nov. 2002, vol. 58, p. 1531-1539).*
Ivarie (Trends in Biotechnology, Jan. 2003, vol. 21, p. 14-19).*
Naito (Animal Sci. J., Jun. 2003, vol. 74, p. 157-168).*
Bird Classification/Families of the Eastern US Birds.*
Proudman, 2001, "The quest for transgenic poultry: birds are not mice with feathers" Biotechnology in Animal Husbandry, vol. 5, Kluwer Academic Publishers, p. 283-299.*
Mizuari (Biochemical and Biophysical Res. Comm. Aug. 24, 2001, vol. 286, p. 456-463).*
Chang (Cell Biology International, 1997, vol. 21, No. 8, p. 495-499).*

* cited by examiner

*Primary Examiner*—Michael C. Wilson
(74) *Attorney, Agent, or Firm*—Clark & Elbing LLP

(57) ABSTRACT

The present invention relates to a method for improving the germline transmission efficiency of avian primordial germ cells (PGCs), and methods for producing avian chimeras and transgenic using it. The present method comprises the steps of (a) isolating primordial germ cells (PGCs) from an avian embryonic gonad; and (b) culturing said PGCs in vitro for at least 5 days. According to the present method, the germline transmission efficiency of PGCs can be dramatically improved in a feasible manner.

8 Claims, 2 Drawing Sheets

METHOD FOR IMPROVING GERMLINE TRANSMISSION EFFICIENCY OF AVIAN PRIMORDIAL GERM CELLS

CROSS-REFERENCE TO RELATED APPLICATIONS

This application claims priority under 35 U.S.C. § 371 from international application PCT/KR2004/000908, filed Apr. 21, 2004, which claims priority under 35 U.S.C. § 119 from Korean Patent Application 10-2003-0025158, filed Apr. 21, 2003.

BACKGROUND OF THE INVENTION

1. Field of the Invention

The present invention relates to a method for improving the germline transmission efficiency in aves, more particular, to a method for improving the germline transmission efficiency of avian primordial germ cells (PGCs), and methods for producing avian chimeras and transgenic using it.

2. Description of the Related Art

The migration pattern of avian primordial germ cells is very different from that of mammals and this unique mode allows producing germline chimeras by the injection of primordial germ cells into the blood vessel of recipient embryos. Primordial germ cells, which are the progenitors of functional gametes after sexual maturity, first originate from the epiblast in the blastoderm and translocate to the hypoblast of the area pellucida (1,2). During the gastrulation, they circulate through the vascular system and finally colonize into the gonadal anlagen (3). Previous reports showed that the transfer of primordial germ cells collected from germinal crescent (4,5) or blood vessel (6) into recipient embryos could produce germline chimeras. However, the number of primordial germ cells provided for transplantation was extremely limited when collected from those embryonic tissues.

It has been known that primordial germ cells lose their migration activity after settling down into the gonad. Chang et al. (7) reported, however, that primordial germ cells from the embryonic gonads, which have passed beyond the migration stage, could also induce germline transmission after being transferred into the recipient embryos at the migratory stage.

As a potent bioreactor, transgenic avian might be more applicable to biotechnology and medicine than transgenic mammals (8). Since avian germ cells migrate into the embryonic gonads through the vascular system, germ cell-mediated germline chimeras have been considered as one of the efficient tools for inducing avian transgenesis. Several attempts were made for producing chicken germline chimera to date (6, 9, 10) and a gonadal primordial germ cell (gPGC) transplantation system has been developed for overcoming a lot of difficulties in the production of transgenic poultry (7, 11, 12). Our previous study (7) first reported the germline chimera production by transfer of chicken gPGCs, which confirmed that primordial germ cells nested in the embryonic gonads could regain migration activity by transplantation into the embryos at earlier stage. However, the germline transmission efficiency remained low leveling the previous study. Therefore, there remains a need in the art for improving germline transmission efficiency in gPGC-derived chicken chimeras.

Throughout this application, various patents and publications are referenced and citations are provided in parentheses. The disclosure of these patents and publications in their entities are hereby incorporated by references into this application in order to more fully describe this invention and the state of the art to which this invention pertains.

SUMMARY OF THE INVENTION

Endeavoring to produce avian chimeras with higher efficiency through improving the germline transmission efficiency of avian primordial germ cells, the present inventors have discovered that PGCs cultured in vitro for a suitable period of time permits to produce germline avian chimeras with higher efficiency.

Accordingly, it is an object of this invention to provide a method for improving the germline transmission efficiency of avian primordial germ cells (PGCs).

It is another object of this invention to provide a method for producing avian germline chimeras exhibiting the improved germline transmission efficiency.

It is still another object of this invention to provide a method for preparing a transgenic avian exhibiting the improved germline transmission efficiency.

Other objects and advantages of the present invention will become apparent from the detailed description to follow taken in conjugation with the appended claims and drawings.

DETAILED DESCRIPTION OF THIS INVETNION

Figure 1:
FIG. 1 is a photograph showing the morphology of gonadal primordial germ cells (gPGCs) cultured on chicken gonadal stroma feeder cell layer. (A) after Ficoll treatment without culture, (B) culture for 5 days, and (C) culture for 10 days. Cultured gPGCs initiated to form cell colony from 7 days after culture and rigid cell cluster was established on the feeder cell layer until the end of culture. The characterization of gPGC colony was undertaken by SSEA-1 staining (arrow heads). No typical sign of cell degeneration was seen and gPGC colonies grew continuously and slowly along the confluent feeder cell layer throughout the culture (magnification ×300).
Figure 1:
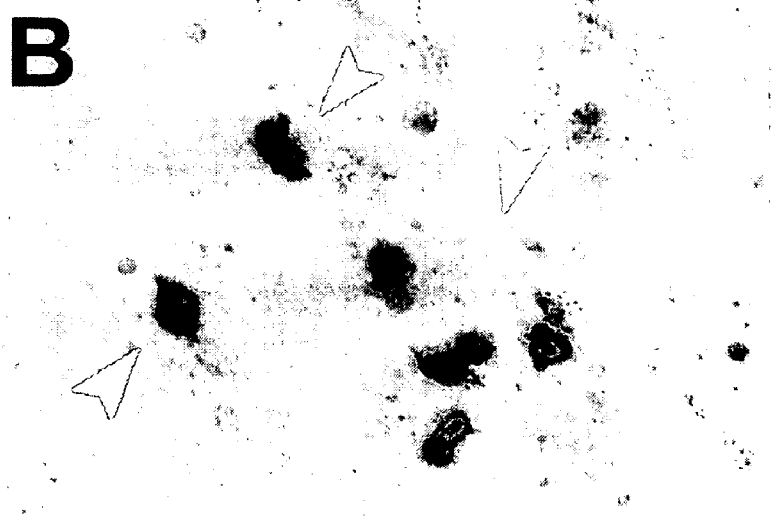
Figure 1:
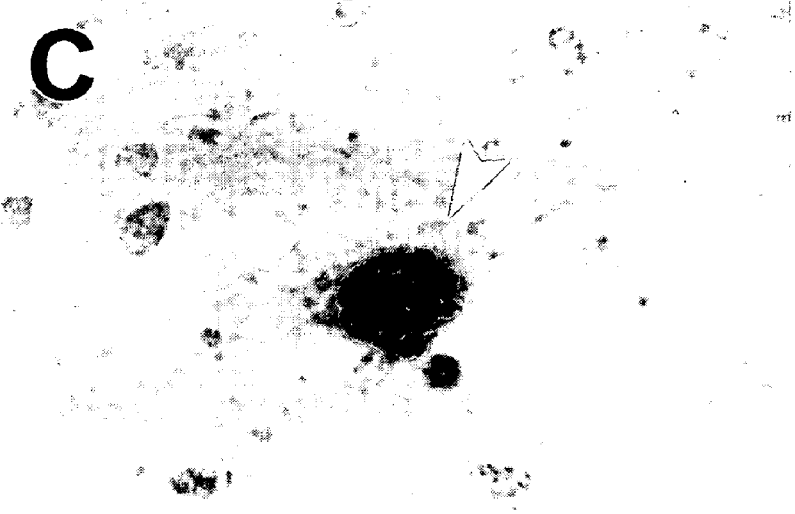
Figure 2:
FIG. 2 is a photograph representing (A) White Leghorn (WL) produced by transfer of gonadal primordial germ cells (gPGCs) of 5.5-day-old Korean Ogol chicken (KOC) embryos. gPGCs were transferred after 10-days culture and no Ficoll treatment was done before transfer. Male WL was proven as a germline chimera in testcross analysis, which mating with female KOC. (B) The hatched progenies from a germline chimera in testcross analysis. Black feather chickens from WL indicated that they are derived from transferred donor gPGCs and white chickens mean hybrids between WL and KOC.
Figure 2:

In one aspect of this invention, there is provided a method for improving the germline transmission efficiency of avian primordial germ cells (PGCs), which comprises the steps of: (a) isolating primordial germ cells (PGCs) from an avian embryonic gonad; and (b) culturing said PGCs in vitro for at least 5 days.

For the production of avian transgenics or chimera using primordial germ cells, the present inventors have made intensive research to improve the germline transmission efficiency in avian transgenics or chimera finally produced, and as a result, surprisingly discovered that PGCs cultured in vitro for a suitable period of time allow avian chimera to show improved germline transmission efficiency.

The term "germline transmission" used herein refers to the transmission of PGCs injected to recipient embryo to its progenitors.

The subject of this invention includes any avian species, preferably, a chicken, a quail, a turkey, a duck, a goose, a pheasant or a pigeon, more preferably, a chicken or a quail, most preferably, a chicken.

Primordial germ cells useful in this invention may be prepared from various sources, most preferably, avian embryonic gonad. Where avian embryo is employed as PGC source, a donor embryo at the stage of about 24-36 (about 4-10 days of incubation), most preferably, at the stage of about 28 (about 5.5 days of incubation) is used. PGCs may be prepared using gonad in various manners, disclosed particularly in Korean Pat. Nos. 0305715 and 0267633 filed by the present inventors. For example, gonads are retrieved from embryos of removed yolk and isolated by the treatment of protease (e.g., trypsin). The preparation of PGCs obtained thus is a population of several cell species including stroma cells as well as PGCs. The term "gonadal cells used herein refers to a population of all cell species existing in gonad. In addition, the term "gonadal primordial germ cells" used herein means one type of gonadal cells to develop to germ cells, abbreviated as "gPGCs".

The most striking feature of this invention lies in the employment of PGCs cultured in vitro for a suitable period of time, i.e., at least 5 days. According to a preferred embodiment, the in vitro culture of PGCs is conducted for at least for 8 days, more preferably, at least for 10 days. Avian chimera or transgenic produced using gPGCs cultured in vitro exhibit dramatically improved germline transmission efficiency.

The medium useful in the in vitro culture of PGCs includes any conventional medium for animal cell culture. Preferably, the in vitro culture of PGCs is performed in a medium containing a cell growth factor and a differentiation inhibitory factor. It is preferred that the cell growth factor used in the medium includes stem cell factor, fibroblast growth factor, interleukin-11, insulin-like growth factor and their combination. Preferably, the differentiation inhibitory factor is leukemia inhibitory factor. In addition, the in vitro culture of PGCs is preferably conducted in a medium containing a serum selected from the group consisting of avian serum (e.g., chicken serum), mammalian serum (e.g., bovine fetal serum) and their combination. In addition to this, the medium used in the in vitro culture of PGCs may contain sodium pyruvate, β-mercaptoethanol and the like.

According to a preferred embodiment, the in vitro culture of PGCs is conducted on a gonadal stroma feeder cell layer. PGCs adhered to the feeder cell layer proliferate and finally form colonies.

PGCs in vitro cultured in step (b) express a stage specific embryonic antigen-1 (SSEA-1) indicative of PGCs.

PGCs having much more improved efficiency in germline transmission, prepared according to the present invention, allow avian chimera or transgenic produced to exhibit improved germline transmission efficiency. In this regard, the most prominent feature of this invention is to prepare PGCs for improving germline transmission efficiency in avian chimera or transgenics, rather than to improve the production efficiency of avian chimera. The improvement in germline transmission efficiency may be due to the suggestion that in vitro culture could drive gPGCs reprogrammed for adapting to gonadal environment after transfer.

The present method is excellent in view of the feasibility and improvement in germline transmission efficiency. In addition, the present method permits to provide an efficient production system of germline chimeras by use of gPGCs, which has not been successful in the art.

In another aspect of this invention, there is provided a method for preparing an avian germline chimera exhibiting the improved germline transmission efficiency, which comprises the steps of: (a) isolating primordial germ cells (PGCs) from an avian embryonic gonad; (b) culturing said PGCs in vitro for at least 5 days; (c) injecting said cultured PGCs into a recipient embryo; and (d) incubating and hatching an egg containing said recipient embryo, whereby the avian germline chimera is prepared.

In still another aspect of this invention, there is provided a method for preparing a transgenic avian exhibiting the improved germline transmission efficiency, which comprises the steps of: (a) isolating primordial germ cells (PGCs) from an avian embryonic gonad; (b) transferring a foreign gene to said PGCs; (c) culturing said transformed PGCs in vitro for at least 5 days; (d) injecting said cultured PGCs into a recipient embryo; and (e) incubating and hatching an egg containing said recipient embryo, whereby the transgenic avian is prepared.

Since, these two methods follow the present method for preparing PGCs with improved germline transmission efficiency, the common descriptions of them are intended to omit in order to avoid the undue redundancy leading to the complexity of this specification.

According a preferred embodiment, the validation of whether cells cultured in vitro are PGCs is performed before injecting cultured cells into recipient embryo. Such validation may be carried out by immunostaining. For example, Solter and Knowles (13) have reported the immunostaining by use of anti SSEA-1 antibody.

The injection of cultured PGCs into recipient embryo may be according to a variety of procedures, preferably, by injecting PGCs into the dorsal aorta of recipient embryo. For example, the cell suspension containing the suitable number of PGCs is injected into the dorsal aorta of recipient embryo using a micropipette and the egg window is sealed, followed by incubating for a suitable period of time. The recipient embryo at various developmental stages may be used, preferably, at the stage of about 13-19 (about 2-2.5 days of incubation), more preferably, at the stage of about 19 (about 2.5 days of incubation).

According to a preferred embodiment, the transfer of the foreign gene to PGCs is carried out by liposome-mediated transfection or electroporation. The electroporation for introducing foreign gene to PGCs is preferably performed according to the procedures suggested by the present inventors (see, Korean Pat. No. 305715).

It has generally accepted that Ficoll gradient separation contributes to increasing the population ratio of PGCs for effective injection into the recipient embryo (14). Several previous reports showed that the positive effect of Ficoll treatment on the separation of PGCs and its safety on maintaining cell viability. However, the data in Examples described below clearly demonstrated that except for the transplantation of 0 day-cultured gPGCs, no beneficial effect of Ficoll separation on the germline transmission efficiency of PGCs was found in our developed system. On the contrary, Ficoll separation negatively affected the germline transmission in the present method. Accordingly, it could be recognized that the present invention could completely avoid the need for Ficoll treatment, enabling the production of avian chimeras or transgenics to become simplified and feasible.

According to a preferred embodiment, the foreign gene contains an antibiotic-resistant gene as a selective marker. It is preferred that the present method further comprises the step of selecting PGCs showing the antibiotic resistance property after step of (c) and the step of (d) is conducted using the antibiotic resistant PGCs. The selective marker useful in this invention may include any gene conferring antibiotic resistance to eukaryotic cells, for example, neomycin-, puromycin- and zeomycin-resistant genes. Where using the selective marker, the medium for the in vitro culture contains antibiotic for selection.

According to the present method for producing avian chimeras or transgenics, the germline transmission efficiency could be dramatically improved.

The following specific examples are intended to be illustrative of the invention and should not be construed as limiting the scope of the invention as defined by appended claims.

EXAMPLES

Methods

I. Retrieval and Culture of gPGCs

Primordial germ cells were retrieved from the gonads of Korean Ogol Chicken (KOC) embryos at the stage 28 (5.5 days of incubation). Stage 28 embryos were rinsed with calcium and magnesium-free PBS for yolk removal and the gonads were retrieved from the embryos by dissecting the abdomen with sharp tweezers under a stereomicroscope. Gonadal tissues were then dissociated by gentle pipetting in 0.05% (v/v) trypsin solution supplemented with 0.53 mM EDTA. After centrifuged at 200×g for 5 minutes, $1 \times 10^4$ cells isolated from the gonadal tissues were seeded onto 96-well culture plate, according to our standard protocol (15). Since preliminary data showed approximately 1% of seeded gonadal cells was gPGC, the number of gPGCs seeded initially into one well was at the range of 100 to 120. Seeded cells were then cultured in Dulbecco's minimal essential medium (Gibco BRL, Grand Island, N.Y.) supplemented with 10% (v/v) fetal bovine serum (FBS; Gibco BRL), 2% (v/v) chicken serum (Gibco BRL), 1 mM sodium pyruvate (Sigma Co, St Louis, Mo.), 55 µM β-mercaptoethanol (Sigma), 20 ng/ml conalbumin (Sigma), 10 mM Hepes (Gibco BRL), 1×antibiotics-antimycotics (Sigma), 5 ng/ml human stem cell factor (hSCF; Sigma), 5 units/ml murine leukemia inhibitory factor (mLIF; Sigma), 10 ng/ml bovine basic fibroblast growth factor (bFGF; Sigma), 0.04 ng/ml human interleukin-11 (hIL-11; Sigma) and 10 ng/ml human insulin-like growth factor-I (hIGF-I; Sigma). The isolated gPGCs were then maintained in a $CO_2$ incubator at 37° C. for 5 or 10 days.

II. Characterization of gPGCs

Stage specific embryonic antigen-1 (SSEA-1) staining was used for the detection of gPGCs. The anti SSEA-1 antibody developed by Solter and Knowles (13) was obtained from the Developmental Studies Hybridoma Bank developed under the auspices of the NICHD and maintained by the University of Iowa. gPGCs in the cell suspension were fixed with 1% (v/v) glutaraldehyde for 5 minutes and rinsed with 1×PBS twice. The anti-SSEA-1 ascites fluid diluted 1:1,000 in PBS was added and subsequent steps were carried out using DAKO universal LSAB° kit, Peroxidase (DAKO, USA) according to the manufacturer's instruction.

III. Transplantation of gPGCs into Recipient Embryos

To examine a potential to differentiate into the germ cell lineage in vivo, 0-, 5- and 10-day cultured KOC gPGCs were injected into the dorsal aorta of White Leghorn (WL) recipient embryos at the stage 17 (2.5 days of incubation). According to the experimental design, Ficoll separation using 10% (v/v) and 16% (v/v) gradient concentration was done prior to the transplantation. For gPGC transfer, a small window was made on the sharp end of recipient egg and approximately 2 to 3 µl of cell suspension containing 150 to 200 gPGCs was injected into the dorsal aorta of recipient embryo using a micropipette. The egg window of the recipient embryo was sealed twice with paraffin film and then laid down with the pointed end at the bottom until hatching.

IV. Testcross Analysis

Hatched chickens were maintained for up to 6 months with our standard management program (7). Sexual maturity of hatched chickens was then monitored by the criterion whether each flock could produce egg or semen. All sexually matured chickens were then provided for testcross analysis by artificial insemination with adult KOCs. The feather color of KOC is black because of the recessive pigmentation gene (i/i) and that of WL is white due to the dominant pigmentation inhibitory gene (I/I). Therefore, the birth of the progenies with black color feather hatched from manipulated WL in the testcross analysis demonstrated that injected gPGCs of KOC had normally proliferated and differentiated in the recipient WL embryos.

V. Experimental Design

Either prospective (culture duration and Ficoll treatment) or retrospective (chimera sexuality) analysis were undertaken to evaluate each treatment effect. For the prospective approach, gPGCs collected from KOC embryos at the stage 28 (5.5-day-old) were randomly allotted into 5 different treatments; 1) collection and transfer simultaneously after Ficoll separation (0 day culture) into recipient embryos, 2) culture for 5 days then transfer after Ficoll treatment, 3) culture for 5 days then transfer without Ficoll treatment, 4) culture for 10 days then transfer after Ficoll treatment and 5) culture for 10 days then transfer without Ficoll treatment. In the prospective assignment, the transfer of 0 day-cultured gPGCs without Ficoll separation was excluded, since gPGC isolation from the gonadal stroma tissue immediately after collection could be made only after Ficoll treatment due to its low population in the collected tissue less than 1%. A crossbred chimera production system was employed for evaluating the effect of each treatment on the production of germline chimeras and their germline transmission efficacy. Retrospective data on chimera sexuality were subsequently combined with the prospective designation. Obtained values from the whole sets of experimental parameter were then subjected to ANOVA using the general linear model (PROC-GLM) in SAS program (16). When the significance of the main effects was detected in each experimental parameter, treatment effects were subsequently compared by the least square method. Significant difference among treatments was determined where the P value was less than 0.05.

Results

I. General Aspects of gPGC Culture with Gonadal Stroma Cells

For the culture of gPGCs, chicken gonadal stroma cells were used as a feeder cell layer and mixed population of gonadal stroma cells and gPGCs in the embryonic gonads were concomitantly seeded into culture dish. The stromal cells quickly proliferated and formed a confluent monolayer within 5 days after seeding, while gPGCs proliferated slowly on gonadal stroma feeder cell layer and formed colonies 7 days after culture (FIG. 1). The colonies firmly adhered to the confluent stromal cell layer, and no signs on cell degeneration such as dispatch from the cell layer could be seen throughout the culture. gPGC colonies expressed the stage specific embryonic antigen (SSEA)-1 epitope during culture, which indicated typical characteristics of primordial germ cells.

II. Treatment Effects on Germline Chimera Production

One hundred fifty to 200 gPGCs per recipient were injected and a total of 683 chickens were hatched after gPGC injection. After management up to 6 months, 301 (44.1%) were sexually matured and subsequently provided for testcross analysis.

TABLE I

Birth of germline chimeras by transfer of chicken gonadal primordial germ cells prepared from different culture durations and separation procedures

| Duration of in vitro culture (days) | With (+) or without (−) Ficoll separation | No. of hatched chickens sexually matured[a] | No. (%)[b] of germline chimeras produced |
|---|---|---|---|
| 0 | + | 39 | 2 (5.1) |
| 5 | + | 35 | 4 (14.4) |
|  | − | 74 | 8 (10.8) |
| 10 | + | 91 | 6 (6.6) |
|  | − | 62 | 7 (11.3) |
| Total |  | 301 | 27 (9.0) |

Model effect of treatment on the number of germline chimera, which is indicated as p value, was 0.6831.
[a]Only sexually-matured chickens were provided for testcross analysis.
[b]Percentage of the number of germline chimeric chickens undertaken testcross analysis.

As shown in Table I, 27 chickens consisting of 15 males and 12 females were proven to be a germline chimera in the progeny test. The proportion of the chimeras to sexually matured chickens was 9.0% (27/301). The range of germline chimerism in each treatment was within 5.1% and 14.4%, and no significant (p=0.6831) treatment effect was found in chimera production. These results indicated that production efficiency of germline chimera was not affected by our experimental treatments.

III. Treatment Effects on the Efficacy of Germline Transmission in Sexually Matured Chimeras We then conducted another comparison for evaluating whether designated treatments affected the efficiency of germline transmission. Although the factorial design of each treatment consisting of both prospective and retrospective assignments was made, total treatments became 9; the groups of 0 day culture only include Ficoll treatment and only male chimeras were produced by transfer of 0 day-cultured gPCGs after Ficoll treatment. Due to such incomplete factorial assignment, a completely block design was employed for statistical analysis.

TABLE II

Induction of germline transmission in produced chimeras of different sexuality after transfer of chicken gonadal primordial germ cells prepared from different culture durations and separation procedures.

| | Systems of germline chimera production | | No. of chickens | | |
|---|---|---|---|---|---|
| Culture duration (days) | With (+) or without (−) Ficoll separation | Sexuality of chimeras | proved as germline chimera | No. of chickens hatched | No. (%)[a] of donor-derived KOCs prduced |
| 0 | + | Male | 2 | 684 | 4 (0.6)[b] |
| 5 | + | Male | 3 | 664 | 10 (1.5)[b] |
| 5 | + | Female | 1 | 59 | 1 (1.7)[bc] |
| 5 | − | Male | 5 | 269 | 21 (7.8)[cd] |
| 5 | − | Female | 3 | 107 | 3 (2.8)[bc] |
| 10 | + | Male | 2 | 639 | 162 (25.4)[e] |
| 10 | + | Female | 4 | 291 | 31 (10.7)[d] |
| 10 | − | Male | 3 | 185 | 92 (49.7)[f] |
| 10 | − | Female | 4 | 376 | 168 (44.7)[f] |

Model effect of treatment on germline transmission, which is indicated as p value, was 0.0001.
[a-f]Percentage of the number of hatched chickens, which indicate the donor-derived progenies.
Different superscripts in the number of produced donor-derived Korean Ogol chickens (KOCs) were significantly different, $p < 0.05$.

As shown in Table II, a significant (p<0.0001) model effect was found. The efficacy of germline transmission was greatly improved as cultured duration increased (0.6%, 1.5 to 7.8% and 10.7 to 49.7% in 0, 5 and 10 day-culture regime, respectively). Within the same in vitro culture duration, improved efficacy of germline transmission was found in no Ficoll-treated group, compared with Ficoll-treated group. Such effect was prominent in the groups of 10-day culture; significant (p<0.0001) increase in germline transmission, regardless of chimera sexuality, was found (44.7 to 49.7% vs. 10.7 to 25.4%). Immunohistochemical assay using anti SSEA-1 antibody showed that no difference in gPGC population in cell suspension was found between with and without Ficoll treatment. So, additional effort to retrieve enough number of gPGCs for transplantation such as increasing the population of gPGCs was not necessary in no-Ficoll treatment groups. Sexuality of chimera did not affect the transmission efficacy; no significant (p=0.6011) difference was found between different sexualities under the same culture duration and separation treatment, except for the group of a 10-day culture with Ficoll treatment. Induction of germline transmission in each individual chimera originated from different gPGC preparation systems was additionally shown in Table III.

tions thereof falling within the spirit of the invention may become apparent to those skilled in this art, and the scope of this invention is to be determined by appended claims and their equivalents.

REFERENCES

1. Hamburger V, Hamilton H L. A series of normal stages in the development of the chick embryo. J Morphol 1951; 88:49-92.
2. Swift C H. Origin and early history of the primordial germ cells in the chick. Am J Anat 1914; 15:483-516.
3. Nieuwkoop P D, Sutasurya L A. The migration of the primordial germ cells. In Primordial Germ Cells in the Chordates. London: Cambridge University Press; 1979: 113-127.
4. Wentworth B C, Tsai H, Hallett J H, Gonzales D S, Rajcic-spasojevic G. Manipulation of avian primordial germ cells and gonadal differentiation. Poultry Sci 1989; 68:999-1010.
5. Jeong D K, Park T S, Kim D K, Song K D, Hong Y H, Han J Y. Production of germline chimeric chickens using primordial germ cells from germinal crescent and blood. Kor J Anim Sci 1999; 41:621-628.
6. Naito M, Tajima A, Yasuda Y, Kuwana T. Production of germline chimeric chickens, with high transmission rate of

TABLE III

Individual efficacy of germline transmission in each germline chimera produced by transfer of chicken gonadal primordial germ cells prepared from different culture durations and separation procedures.

| Culture duration (days) | With (+) or without (−) Ficoll treatment | Sexuality of chimeras | ID no. of germline chimeras | No. of chickens hatched | No. (%)[a] of donor-derived KOCs produced |
|---|---|---|---|---|---|
| 0 | + | Male | 001 | 342 | 2 (0.6) |
| 0 | + | Male | 011 | 342 | 2 (0.6) |
| 5 | + | Male | 501 | 332 | 3 (0.9) |
| 5 | + | Male | 502 | 35 | 1 (2.9) |
| 5 | + | Male | 503 | 297 | 6 (2.0) |
| 5 | + | Female | 513 | 59 | 1 (1.7) |
| 5 | − | Male | 505 | 65 | 1 (1.5) |
| 5 | − | Male | 510 | 78 | 1 (1.3) |
| 5 | − | Male | 511 | 40 | 1 (2.5) |
| 5 | − | Male | 554 | 54 | 9 (16.7) |
| 5 | − | Male | 568 | 32 | 9 (28.1) |
| 5 | − | Female | 515 | 32 | 1 (3.1) |
| 5 | − | Female | 547 | 40 | 1 (2.5) |
| 5 | − | Female | 560 | 35 | 1 (2.9) |
| 10 | + | Male | A27 | 334 | 6 (1.8) |
| 10 | + | Male | A32 | 305 | 156 (51.1) |
| 10 | + | Female | A34 | 45 | 1 (2.2) |
| 10 | + | Female | A40 | 88 | 2 (2.3) |
| 10 | + | Female | A43 | 65 | 27 (41.5) |
| 10 | + | Female | A44 | 93 | 1 (1.1) |
| 10 | − | Male | B01 | 25 | 14 (56.0) |
| 10 | − | Male | B04 | 16 | 1 (6.3) |
| 10 | − | Male | B17 | 144 | 77 (53.5) |
| 10 | − | Female | C01 | 92 | 52 (56.5) |
| 10 | − | Female | C04 | 98 | 38 (38.8) |
| 10 | − | Female | C05 | 37 | 2 (5.4) |
| 10 | − | Female | C08 | 149 | 76 (51.0) |
| Total | | | | 3,274 | 492 (15.0) |

[a]Percentage of the number of hatched chickens, which indicate the donor-derived progenies.

Having described a preferred embodiment of the present invention, it is to be understood that variants and modificadonor-derived gametes, produced by transfer of primordial germ cells. Mol Reprod Dev 1994; 39:153-161.

7. Chang I K, Jeong D K, Hong Y H, Park T S, Moon Y K, Ohno T, Han J Y. Production of germline chimeric chickens by transfer of cultured primordial germ cells. Cell Biol Int 1997; 8:495-499.
8. Sang H. Transgenic chickens-methods and potential applications. Trends Biotechnol 1994; 12:415-420.
9. Carsience R S, Clark M E, Verrinder Gibbins A M, Etches R J. Germline chimeric chickens from dispersed donor blastodermal cells and compromised recipient embryos. Development 1993; 117:669-675.
10. Pain B, Clark M E, Shen M, Nakazawa H, Sakurai M, Samarut J, Etches R J. Long-term in vitro culture and characterisation of avian embryonic stem cells with multiple morphogenetic potentialities. Development 1996; 122:2339-2348.
11. Chang I, Yoshiki A, Kusakabe M, Tajima A, Chikamune T, Naito M, Ohno T. Germ line chimera produced by transfer of cultured chick primordial germ cells. Cell Biol Int 1995; 19:569-676.
12. Tajima A, Naito M, Yahuda Y, Kuwana T. Production of germ-line chimeras by transfer of cryopreserved gonadal primordial germ cells (gPGCs) in chicken. J Zool 1998; 280:265-267.
13. Solter D, Knowles BB. Monoclonal antibody defining a stage-specific mouse embryonic antigen (SSEA-1). Proc Natl Acad Sci 1978; 75:5565-5569.
14. Yasuda Y, Tajima A, Fujimoto T, Kuwana T. A method to obtain avian germ-line chimeras using isolated primordial germ cells. J Reprod Fertil 1992; 96:521-528.
15. Park T S, Han J Y Derivation and characterization of pluripotent embryonic germ cells in chicken. Mol Reprod Dev 2000; 56:475-482.
16. Anon. SAS Users Guide. Statistics. Cary, NC: Statistical Analysis System Institute; 1992

What is claimed is:

1. A method of improving the ability to prepare germline chimeric chickens, which comprises the steps of:
   (a) isolating primordial germ cells (PGCs) from a chicken embryonic gonad;
   (b) culturing said PGCs in vitro for at least 10 days on a gonadal stroma feeder cell layer such that PGCs that are positive for stage specific embryonic antigen-1 (SSEA-1) are obtained;
   (c) injecting the PGCs that are positive for SSEA-1 into the dorsal aorta of a recipient chicken embryo without prior treatment of said cultured PGCs with Ficoll; and
   (d) incubating and hatching an egg containing the recipient chicken embryo such that a germline chimeric chicken is obtained, wherein the efficiency of germline transmission of the PGCs injected is between 44.7% and 49.7%.

2. The method according to claim 1, wherein said culturing of the PGCs in vitro is conducted in a medium containing a cell growth factor and a differentiation inhibitory factor.

3. The method according to claim 2, wherein said cell growth factor is selected from the group consisting of stem cell factor, fibroblast growth factor, interleukin-11, insulin-like growth factor and their combination.

4. The method according to claim 2, wherein said differentiation inhibitory factor is leukemia inhibitory factor.

5. The method according to claim 1, wherein said culturing of the PGCs in vitro is conducted in a medium containing a serum selected from the group consisting of avian serum, mammalian serum, and their combination.

6. The method of claim 1, wherein the chicken embryonic gonad is a Korean Ogol Chicken (KOC) embryonic gonad.

7. The method of claim 1, wherein the recipient chicken embryo is a White Leghorn embryo.

8. The method of claim 1, wherein the chicken embryonic gonad is a Korean Ogol Chicken (KOC) embryonic gonad and the recipient chicken embryo is a White Leghorn embryo.

* * * * *